(12) United States Patent
Takamatsu et al.

(10) Patent No.: US 9,856,209 B2
(45) Date of Patent: Jan. 2, 2018

(54) XYLYLENE DICARBAMATE, METHOD FOR PRODUCING XYLYLENE DIISOCYANATE, XYLYLENE DIISOCYANATE, AND METHOD FOR RESERVING XYLYLENE DICARBAMATE

(71) Applicant: MITSUI CHEMICALS, INC., Tokyo (JP)

(72) Inventors: Koji Takamatsu, Omuta (JP); Hideki Sone, Machida (JP); Masaaki Sasaki, Yokohama (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/410,221

(22) Filed: Jan. 19, 2017

(65) Prior Publication Data

US 2017/0158623 A1  Jun. 8, 2017

Related U.S. Application Data

(62) Division of application No. 14/781,721, filed as application No. PCT/JP2014/059306 on Mar. 28, 2014, now Pat. No. 9,624,165.

(30) Foreign Application Priority Data

Apr. 3, 2013  (JP) .................................. 2013-077928

(51) Int. Cl.
  *C07C 271/00*  (2006.01)
  *C07C 271/20*  (2006.01)

(52) U.S. Cl.
  CPC .................................. *C07C 271/20* (2013.01)

(58) Field of Classification Search
  CPC ... C07C 271/20; C07C 263/04; C07C 265/14; C07C 269/08; C07C 271/12
  See application file for complete search history.

(56) References Cited

U.S. PATENT DOCUMENTS

| | | | |
|---|---|---|---|
| 3,717,671 A | 2/1973 | Huang et al. | |
| 4,701,549 A | 10/1987 | Mullins | |
| 5,196,572 A | 3/1993 | Okawa et al. | |
| 2005/0043561 A1 | 2/2005 | Michalczak | |
| 2013/0023691 A1 | 1/2013 | Nagasaki | |
| 2013/0109881 A1 | 5/2013 | Murayama et al. | |

FOREIGN PATENT DOCUMENTS

| | | |
|---|---|---|
| CA | 2209754 A | 1/1998 |
| CN | 102933545 | 2/2013 |
| JP | 107641 | 1/1998 |
| JP | 1087598 | 4/1998 |
| JP | 11-005773 | 1/1999 |
| JP | 200086614 | 3/2000 |
| JP | 200568146 | 3/2005 |
| WO | 2011125429 A1 | 10/2011 |

OTHER PUBLICATIONS

International Search Report dated Jun. 17, 2014 issued in PCT/JP2014/059306.
International Preliminary Report on Patentability dated Oct. 15, 2015 filed in PCT/JP2014/059306.
Extended European Search Report dated Nov. 7, 2016 issued in the corresponding European patent application No. 14779939.9.

*Primary Examiner* — Yevegeny Valenrod
*Assistant Examiner* — Blaine G Doletski
(74) *Attorney, Agent, or Firm* — Rankin, Hill & Clark LLP

(57) ABSTRACT

Xylylene dicarbamate contains impurities represented by formulas (1) to (4) below at a ratio of less than 100 ppm as a total amount thereof on a mass basis.

[Chemical Formula 1]

(In the above-described formulas (1) to (4), R represents a monovalent hydrocarbon group.).

1 Claim, 4 Drawing Sheets

XYLYLENE DICARBAMATE, METHOD FOR PRODUCING XYLYLENE DIISOCYANATE, XYLYLENE DIISOCYANATE, AND METHOD FOR RESERVING XYLYLENE DICARBAMATE

TECHNICAL FIELD

The present invention relates to xylylene dicarbamate, a method for producing xylylene diisocyanate using the xylylene dicarbamate, xylylene diisocyanate obtained by the method for producing xylylene diisocyanate, and a method for reserving xylylene dicarbamate capable of reducing an impurity content.

BACKGROUND ART

Conventionally, carbamates (urethane compound) such as xylylene dicarbamate have been a useful organic compound as an industrial material having a wide range of applications such as a material of medicine, agricultural chemicals, and the like; a material of various fine chemicals; and furthermore, an analysis agent of alcohols.

Recently, such carbamates have been variously considered as a production material of an isocyanate without using phosgene.

That is, the isocyanate is an organic compound having an isocyanate group and is widely used as a material of polyurethane. The isocyanate is industrially produced by reaction between amine and phosgene (phosgene method).

However, phosgene is highly toxic, strongly corrosive, and disadvantageous in handling. Thus, as a method for producing an isocyanate instead of the phosgene method, a method for producing an isocyanate by thermally decomposing a urethane compound (carbamate) has been recently considered.

To be specific, for example, a method in which a formamide compound and dimethyl carbonate are allowed to react in the coexistence of methanol to extract the produced methyl formate to the outside of the system by distillation, while the obtained urethane compound is thermally decomposed to obtain an isocyanate compound has been proposed.

Patent Document 1 below has, for example, proposed that in a thermal decomposition reactor of such a urethane compound, a storage tank (material tank) of the urethane compound is in a nitrogen atmosphere and that the obtained urethane compound, when solid at normal temperature, is thermally melted to be stored from the viewpoint of workability at the time of being transported to the thermal decomposition reactor.

Also, as a method for producing an isocyanate instead of the phosgene method, in addition to the above-described method, Patent Document 2 below has, for example, considered a method of producing diisocyanate by synthesizing dicarbamate (urethane compound) by reaction of diamine, alcohol, and urea and/or a urea derivative and thereafter, thermally decomposing the obtained carbamate (urethane compound).

CITATION LIST

Patent Document

Patent Document 1: Japanese Unexamined Patent Publication No. H10-7641

Patent Document 2: Japanese Unexamined Patent Publication No. 2005-68146

SUMMARY OF THE INVENTION

Problem to be Solved by the Invention

Meanwhile, in the production of such an isocyanate, when a carbamate (urethane compound) is stored in a heated state, impurities may be produced by deterioration of the carbamate or the like.

Among all, xylylene diisocyanate, which is araliphatic diisocyanate, has properties of easily producing impurities, compared to another diisocyanate (e.g., alicyclic diisocyanate etc.).

There is a disadvantage that when xylylene dicarbamate containing a large amount of impurities is thermally decomposed, the obtained xylylene diisocyanate yield is decreased.

In this regard, for example, as described in Patent Document 1, by bringing the storage tank of the carbamate into a nitrogen atmosphere, suppressing production of impurities is considered, but there may be a case where production of impurities cannot be sufficiently suppressed by such a method.

An object of the present invention is to provide xylylene dicarbamate in which an impurity content is reduced, a method for producing xylylene diisocyanate using the xylylene dicarbamate, xylylene diisocyanate obtained by the method for producing xylylene diisocyanate, and a method for reserving xylylene dicarbamate that is capable of reducing an impurity content.

Means For Solving the Problem

To achieve the above-described object, xylylene dicarbamate of the present invention contains impurities represented by formulas (1) to (4) below at a ratio of less than 100 ppm as a total amount thereof on a mass basis.

[Chemical Formula 1]

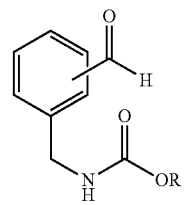

(1)

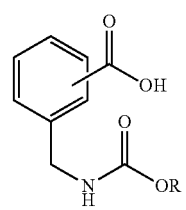

(2)

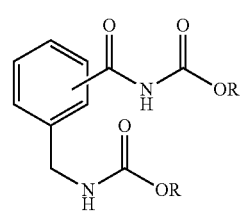

(3)

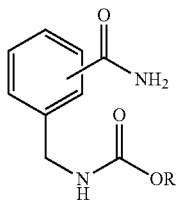

(4)

(In the above-described formulas (1) to (4), R represents a monovalent hydrocarbon group.)

A method for producing xylylene diisocyanate of the present invention obtained by thermally decomposing the above-described xylylene dicarbamate.

Xylylene diisocyanate of the present invention is obtained by the above-described method for producing xylylene diisocyanate.

A method for reserving xylylene dicarbamate of the present invention includes reserving the xylylene dicarbamate containing impurities represented by formulas (1) to (4) below at a ratio of less than 100 ppm as a total amount thereof on a mass basis under heating at 50 to 180° C.

[Chemical Formula 2]

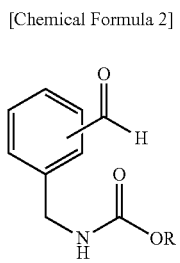

(1)

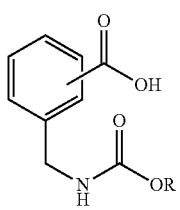

(2)

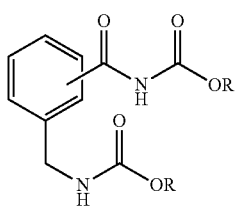

(3)

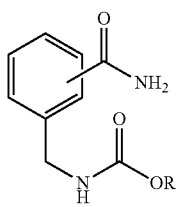

(4)

(In the above-described formulas (1) to (4), R represents a monovalent hydrocarbon group.)

In the method for reserving xylylene dicarbamate of the present invention, it is preferable that a total oxygen amount of an oxygen amount contained in a space portion when xylylene dicarbamate fills a vessel and an oxygen amount dissolved in the xylylene dicarbamate relative to the xylylene dicarbamate is less than 100 ppm.

Effect of the Invention

In xylylene dicarbamate of the present invention, an impurity content represented by the above-described formulas (1) to (4) is less than 100 ppm on a mass basis, so that high quality in various applications is achieved and among all, by thermal decomposition, xylylene diisocyanate can be produced in high yield.

In a method for producing xylylene diisocyanate of the present invention, xylylene dicarbamate of the present invention is used, so that xylylene diisocyanate of the present invention can be obtained in high yield.

In a method for reserving xylylene dicarbamate of the present invention, an impurity content represented by the above-described formulas (1) to (4) is less than 100 ppm on a mass basis under heating, so that a incited state is retained and workability at the time of transportation can be ensured. Furthermore, the reserved xylylene dicarbamate has high quality in various applications and among all, by thermal decomposition, xylylene diisocyanate can be produced in high yield.

DESCRIPTION OF EMBODIMENTS

Figure 1:
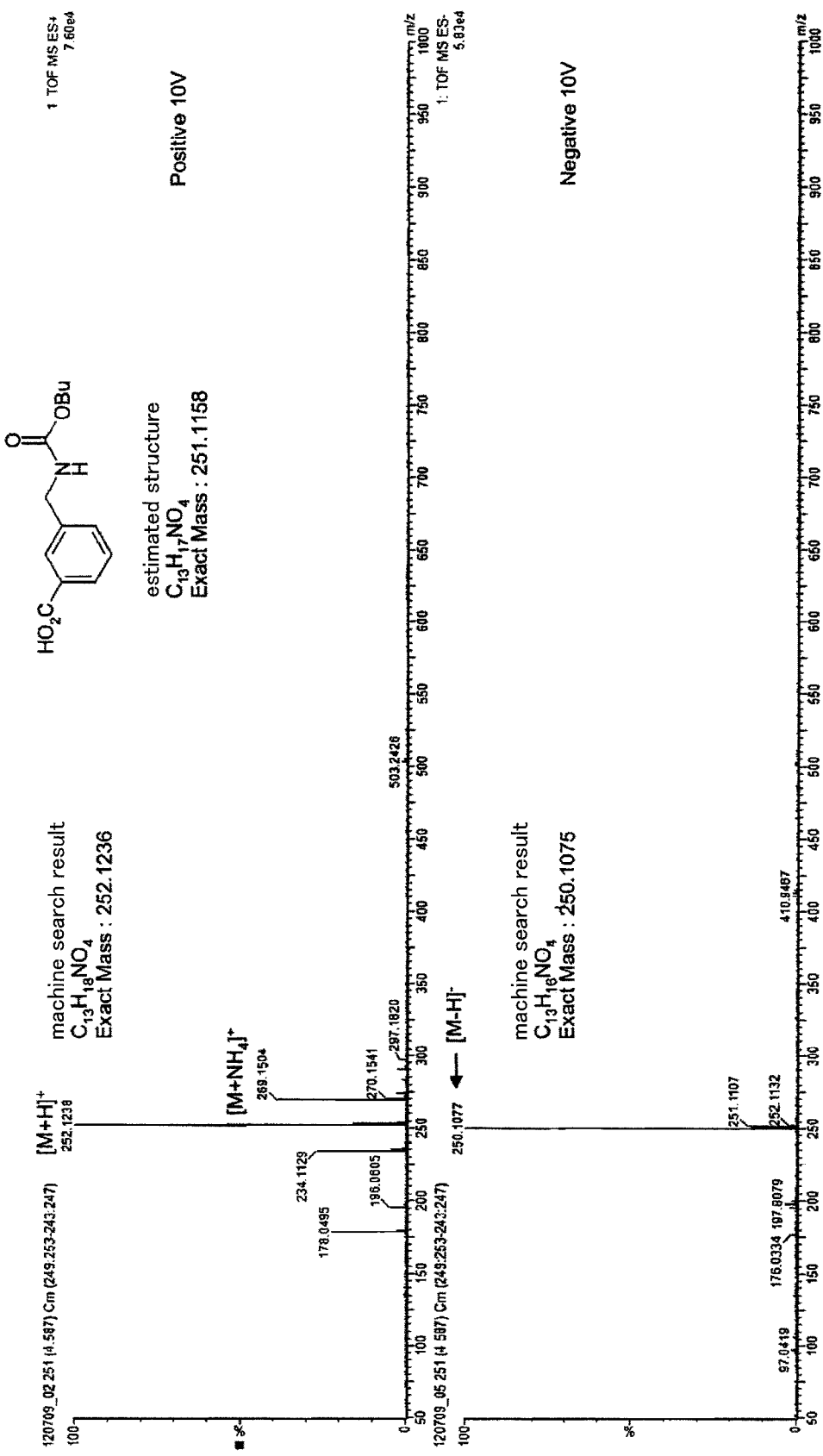
FIG. 1 shows a mass spectrum of the peak exhibited at a retention time of [4.587] in a liquid chromatogram.

In the present invention, examples of xylylene dicarbamate include 1,2-xylylene dicarbamate, 1,3-xylylene dicarbamate, 1,4-xylylene dicarbamate, and a mixture thereof. Preferably, 1,3-xylylene dicarbamate and 1,4-xylylene dicarbamate are used, or more preferably, 1,3-xylylene dicarbamate is used.

The xylylene dicarbamate can be obtained by a known method Without particular limitation. Examples of the known method include a method in which xylylenediamine forms carbamate with dialkyl carbonate (carbonate method) and a method in which xylylenediamine forms carbamate with urea, N-unsubstituted carbamic acid ester, and the like under the presence of alcohol (urea method).

The xylylene dicarbamate is, for example, represented by formula (5) below.

[Chemical Formula 3]

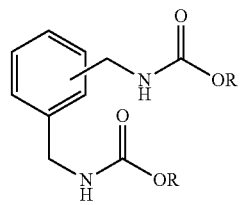

(5)

(In the above-described formula (5), R represents a monovalent hydrocarbon group.)

In the above-described formula (5), examples of the monovalent hydrocarbon group represented by R include an alkyl group and an aryl group.

Examples of the alkyl group include a straight chain or branched saturated hydrocarbon group having 1 to 8 carbon atoms such as methyl, ethyl, n-propyl, iso-propyl, n-butyl, iso-butyl, sec-butyl, tert-butyl, pentyl, hexyl, heptyl, octyl, iso-octyl, and 2-ethylhexyl and an alicyclic saturated hydrocarbon group having 5 to 10 carbon atoms such as cyclohexyl and cyclododecyl.

An example of the aryl group includes an aromatic hydrocarbon group having 6 to 18 carbon atoms such as phenyl, tolyl, xylyl, biphenyl, naphthyl, anthryl, and phenanthryl.

These monovalent hydrocarbon groups may be used singly or in a combination of two or more.

The monovalent hydrocarbon group is preferably an alkyl group, more preferably, a straight chain or branched saturated hydrocarbon group having 1 to 8 carbon atoms, further more preferably, a straight chain or branched saturated hydrocarbon group having 1 to 6 carbon atoms, particularly preferably, a straight chain saturated hydrocarbon group having 2 to 6 carbon atoms.

The monovalent hydrocarbon group may have a substituent. Examples of the substituent include a hydroxyl group, a halogen atom (e.g., chlorine, fluorine, bromine, iodine, etc.), a cyano group, an amino group, a carboxyl group, an alkoxy group (e.g., alkoxy group having 1 to 4 carbon atoms such as methoxy, ethoxy, propoxy, butoxy, etc.), an aryloxy group (e.g., phenoxy group etc.), an alkylthio group (e.g., alkylthio group having 1 to 4 carbon atoms such as methylthio, ethylthio, propylthio, butylthio, etc.), and an arylthio group (e.g., phenylthio group etc.). The substituent replaced with the hydrocarbon group may be single (one piece) or plural (two pieces or more). When a plurality of substituents described above are replaced with the monovalent hydrocarbon group, the substituents may be the same or different from each other. The monovalent hydrocarbon group is preferably a monovalent hydrocarbon group not having a substituent.

These xylylene dicarbamates may be used singly or in a combination of two or more.

The xylylene dicarbamate contains impurities represented by formulas (1) to (4) below.

[Chemical Formula 4]

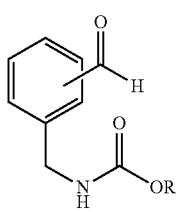

(1)

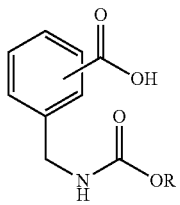

(2)

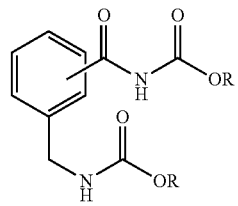

(3)

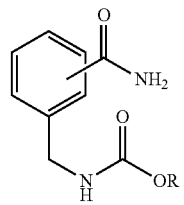

(4)

(In the above-described formulas (1) to (4), R represents a monovalent hydrocarbon group.)

In the above-described formulas (1) to (4), R represents the same monovalent hydrocarbon group as that in the above-described formula (5).

It is presumed that the impurities represented by the above-described formulas (1) to (4) are, for example, a compound (oxide) obtained by oxidizing the above-described xylylene dicarbamate. The compound represented by the above-described formula (1) is referred to as a formyl-benzyl carbamate (aldehyde product). The compound represented by the above-described formula (2) is referred to as a carboxyl-benzyl carbamate (carboxylic acid product). The compound represented by the above-described formula (3) is referred to as a carbonyl carbamate-benzyl carbamate (imide product). The compound represented by the above-described formula (4) is referred to as a carbamoyl-benzyl carbamate (amide product).

An impurity content represented by the above-described formulas (1) to (4) in the xylylene dicarbamate as a total amount thereof on a mass basis is less than 100 ppm, preferably 80 ppm or less, more preferably 40 ppm or less, particularly preferably 10 ppm or less, and usually 1 ppm or more.

When the impurity content is within the above-described range, quality of the xylylene dicarbamate in various applications can be improved and among all, when the xylylene diisocyanate is produced by thermal decomposition, the xylylene diisocyanate yield can be improved.

That is, there is a disadvantage that when the xylylene dicarbamate containing a large amount of impurities is thermally decomposed, the obtained xylylene diisocyanate yield is decreased.

Meanwhile, the above-described xylylene dicarbamate has the impurity content in the above-described range, so that by thermal decomposition, xylylene diisocyanate can be produced in high yield. The impurity content of the xylylene dicarbamate can be obtained with high performance liquid chromatography (HPLC) to be described later or the like.

When the xylylene dicarbamate is used as a production material the xylylene diisocyanate, for example, first, the xylylene dicarbamate reserved in a storage tank is pressure-driven transported to a thermal decomposition apparatus or the like to be then heated and thermally decomposed in the thermal decomposition apparatus. In such a case, the xylylene dicarbamate before thermal decomposition is solid at normal temperature (melting point of, for example, 50 to 150° C., though depending on the number of carbons in the carbamate group), so that it is heated at a predetermined temperature in the storage tank and is reserved in a melted state (flow state) from the viewpoint of workability at the time of transportation.

When the xylylene dicarbamate is reserved under heating, however, impurities represented by the above-described formulas (1) to (4) may be produced by deterioration of the xylylene dicarbamate or the like, depending on the reserving conditions thereof. Thus, when the xylylene dicarbamate is reserved under heating, a reserving method of suppressing production of impurities and being capable of reducing the impurity content in the xylylene dicarbamate is required.

In the following, a method for reserving xylylene dicarbamate capable of suppressing production of impurities is described in detail.

That is, in the method for reserving xylylene dicarbamate, the xylylene dicarbamate is reserved so that it contains the impurities represented by formulas (1) to (4) below at a ratio of less than 100 ppm as a total amount thereof on a mass basis.

The heating conditions of the xylylene dicarbamate are, for example, 50° C. or more, preferably 70° C. or more, more preferably 90° C. or more, and for example, 180° C. or less, preferably 170° C. or less, more preferably 160° C. or less.

When the heating conditions are within the above-described range, the melted state is retained in a range in which the xylylene dicarbamate is not thermally decomposed, and workability at the time of transportation can be improved.

In the method for reserving xylylene dicarbamate, a total oxygen amount of an oxygen amount contained in a space portion when the xylylene dicarbamate fills a vessel and an oxygen amount dissolved in the xylylene dicarbamate relative to the xylylene dicarbamate is less than 100 ppm.

To be more specific, the total oxygen amount of the oxygen amount contained in the space portion when the xylylene dicarbamate fills the vessel and the oxygen amount dissolved in the xylylene dicarbamate relative to the xylylene dicarbamate is less than 100 ppm, preferably 50 ppm or less, more preferably 20 ppm or less, further more preferably 10 ppm or less, and usually 1 ppm or more.

When the oxygen amount is within the above-described range, oxidation of the xylylene dicarbamate can be suppressed and production of impurities represented by the above-described formulas (1) to (4) can be suppressed.

A method for setting the total oxygen amount of the oxygen amount contained in the space portion when the xylylene dicarbamate fills the vessel and the oxygen amount dissolved in the xylylene dicarbamate relative to the xylylene dicarbamate within the above-described range is not particularly limited. Examples of the method include a method in which the storage tank of the xylylene dicarbamate is filled with an inert gas and a method in which the storage tank of the xylylene dicarbamate is subjected to decompression treatment to be evacuated. Preferably, a method in which the storage tank of the xylylene dicarbamate is filled with an inert gas is used.

Examples of the inert gas include rare gas such as helium gas, neon gas, argon gas, and krypton gas and nitrogen gas. Preferably, nitrogen gas is used.

The inert gas has a purity of, for example, above 99.99% by volume, preferably 99.999% by volume or more, and usually 100% by volume or less.

When the purity of the inert gas is within the above-described range, the total oxygen amount of the oxygen amount contained in the space portion and the oxygen amount dissolved in the xylylene dicarbamate relative to the xylylene dicarbamate can be adjusted within the above-described range, so that production of impurities can be suppressed.

That is, when the purity of the inert gas is the above-described lower limit or less (for example, when an industrial nitrogen gas having a purity of 99.99% by volume is used), there may be a case where filling a storage tank with an inert gas cannot sufficiently reduce the total oxygen amount of the oxygen amount contained in the space portion and the oxygen amount dissolved in the xylylene dicarbamate relative to the xylylene dicarbamate, so that a large amount of impurities are produced in the xylylene dicarbamate.

The nitrogen gas generally used as an inert gas in industrial production facilities such as factories is usually industrially produced by a PSA (Pressure Swing Adsorption) method. However, the nitrogen gas obtained by this method has a purity of 99.99% by volume or less, so that filling e storage tank with the nitrogen gas cannot sufficiently reduce the total oxygen amount of the oxygen amount contained in the space portion and the oxygen amount dissolved in the xylylene dicarbamate relative to the xylylene dicarbamate.

Meanwhile, when the purity of the inert gas is within the above-described range, filling the storage tank with the inert gas can sufficiently reduce the total oxygen amount of the oxygen amount contained in the space portion and the oxygen amount dissolved in the xylylene dicarbamate relative to the xylylene dicarbamate, so that production of impurities in the xylylene dicarbamate can be suppressed.

When the storage tank of the xylylene dicarbamate is filled with the inert gas, the aeration rate, the pressure, and the like of the inert gas are not particularly limited and are set suitably in accordance with the purpose and application.

In the method for reserving xylylene dicarbamate, the reserving time of the xylylene dicarbamate in the storage tank is, for example, 72 hours or less, preferably 48 hours or less, more preferably 24 hours or less, and usually 30 minutes or more.

The above-described impurity content with respect to the xylylene dicarbamate reserved by the method for reserving xylylene dicarbamate as a total amount thereof on a mass basis is less than 100 ppm, preferably 80 ppm or less, more preferably 40 ppm or less, particularly preferably 10 ppm or less, and usually 1 ppm or more.

According to the above-described method for reserving xylylene dicarbamate, the impurity content represented by the above-described formulas (1) to (4) can be less than 100 ppm on a mass basis under heating, so that a melted state is retained and workability at the time of transportation can be ensured. Furthermore, the reserved xylylene dicarbamate has high quality in various applications and among all, by thermal decomposition, the xylylene diisocyanate can be produced in high yield.

Thus, the xylylene dicarbamate reserved by the above-described reserving method is preferably used as a production material for producing xylylene diisocyanate by thermal decomposition.

To be specific, in the thermal decomposition of the xylylene dicarbamate, xylylene diisocyanate (1,2-xylylene diisocyanate, 1,3-xylylene diisocyanate, diisocyanate, a mixture thereof, and the like) corresponding to the xylylene dicarbamate and alcohol, which is a by-product, represented by general formula (6) below are produced.

$$R-OH \tag{6}$$

(where R is the same as that in the above-described formulas (1) to (4).)

The thermal decomposition is not particularly limited and for example, any known decomposition method such as a liquid phase method or a vapor phase method can be used.

In the vapor phase method, the xylylene diisocyanate and the alcohol obtained by the thermal decomposition can be separated from a gaseous product mixture by fractional condensation. In the liquid phase method, the xylylene diisocyanate and the alcohol obtained by the thermal decomposition can be separated, for example, by distillation or using a solvent and/or inert gas as a support substance.

As the thermal decomposition, a liquid phase method is preferable from the viewpoint of workability.

In such a method, the xylylene dicarbamate is thermally decomposed preferably in the presence of an inert solvent.

The inert solvent is not particularly limited as long as it dissolves at least the xylylene dicarbamate, is inert to the xylylene dicarbamate and the xylylene diisocyanate, and remains unreacted (i.e., stable) during the thermal decomposition. For efficient thermal decomposition reaction, the inert solvent preferably has a higher boiling point than the xylylene diisocyanate to be obtained.

The inert solvent is suitably selected in accordance with, for example, number of carbons of the xylylene dicarbamate, pressure conditions, or the like, and for example, aromatic hydrocarbons may be used.

Examples of the aromatic hydrocarbons include benzene (boiling point: 80° C.), toluene (boiling point: 111° C.), o-xylene (boiling point: 144° C.), m-xylene (boiling point: 139° C.), p-xylene (boiling point: 138° C.), ethylbenzene (boiling point: 136° C.), isopropylbenzene (boiling point: 152° C.), butylbenzene (boiling point: 185° C.), cyclohexylbenzene (boiling point: 237 to 340° C.), tetralin (boiling point: 208° C.), chlorobenzene (boiling point: 132° C.), o-dichlorobenzene (boiling point: 180° C.), 1-methylnaphthalene (boiling point: 245° C.), 2-methylnaphthalene (boiling point: 241° C.), 1-chloronaphthalene (boiling point: 263° C.), 2-chloronaphthalene (boiling point: 264 to 266° C.), triphenylmethane (boiling point: 358 to 359° C. (754 mmHg)), 1-phenylnaphthalene (boiling point: 324 to 325° C.), 2-phenylnaphthalene (boiling point: 357 to 358° C.), biphenyl (boiling point: 255° C.), and dibenzyltoluene (boiling point: 391° C.).

These solvents are also available as commercially available products and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 2H (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove, manufactured by Matsumura Oil Co., Ltd.) and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KS K-OIL 280 (aromatic hydrocarbon, boiling point: 303° C.) (hereinabove, manufactured by Soken Tecnix Co., Ltd.).

Examples of the inert solvent also include esters (e.g., dioctyl phthalate, didecyl phthalate, didodecyl phthalate, etc.) and aliphatic hydrocarbons regularly used as a heating medium.

These examples of the inert solvent can be used singly or in a combination of two or more.

The inert solvent is blended in an amount in the range of 0.001 to 100 parts by mass, preferably 0.01 to 80 parts by mass, more preferably 0.1 to 50 parts by mass relative to 1 part by mass of the xylylene dicarbamate.

In the thermal decomposition, for example, the inert solvent is blended in the xylylene dicarbamate to thermally decompose the xylylene dicarbamate, and thereafter, the inert solvent is separated and recovered, to be blended in the xylylene dicarbamate again in thermal decomposition.

The reaction conditions for the thermal decomposition reaction are suitably set: for example, the thermal decomposition temperature of usually 350° C. or less, preferably 80 to 350° C., more preferably 100 to 300° C. The thermal decomposition temperature of lower than 80° C. may fail to achieve practical reaction rate, and furthermore, the thermal decomposition temperature of more than 350° C. may cause disadvantageous side reactions, such as polymerization of xylylene diisocyanate. The pressure at the time of thermal decomposition reaction is preferably a pressure that allows for vaporization of the obtained alcohol with the above-described thermal decomposition reaction temperature, and in terms of equipment and utilities, practically, the pressure at the time of thermal decomposition reaction is preferably 0.133 to 90 kPa.

In his method, as necessary, a catalyst can be further added.

The catalyst can be added at, although the timing can be different depending on the types of the catalyst, any time of the following: the time of the above-described reaction, before and after the distillation separation after the reaction, and before and after the separation of the xylylene dicarbamate.

As the catalyst used in the thermal decomposition, one or more metal substance selected from Sn, Sb, Fe, Co, Ni, Cu, Cr, Ti, Ph, Mo, and Mn; or a metal compound such as oxide, halide, carboxylate, phosphate, and an organic metal compound of these used in urethane reaction between xylylene diisocyanate and hydroxyl groups is used. Of these examples of catalysts, because Fe, Sn, Co, Sb, and Mn exhibit effects of suppressing by-products, they are preferably used in the thermal decomposition.

Examples of the metal catalysts of Sn include tin oxide, tin chloride, bromide, tin iodide, tin formate, tin acetate, tin oxalate, tin octylate, tin stearate, tin oleate, tin phosphate, dibutyltin dichloride, dibutyltin dilaurate, and 1,1,3,3-tetrabutyl-1,3-dilauryloxydistannoxane.

Examples of the metal catalysts of Fe, Co, Sb, and Mn include acetate, benzoate, naphthenate, and acetylacetonato salt thereof.

The mixing amount of the catalyst, as a metal substance or a compound thereof, relative to the reaction liquid is in the range of 0.0001 to 5 mass %, preferably in the range of 0.001 to 1 mass %.

In the thermal decomposition reaction, as necessary, a stabilizer can also be blended.

Examples of the stabilizer include o-toluene sulfonamide and p-toluene sulfonamide, and they may be used singly or in a combination of two or more.

The mixing ratio of the stabilizer is not particularly limited and is set suitably in accordance with the purpose and application.

The thermal decomposition reaction can be conducted in any of the batch reaction, in which xylylene dicarbamate, a catalyst, and an inert solvent are charged at once, and the continuous reaction, in which xylylene dicarbamate is charged in an inert solvent containing a catalyst under reduced pressure.

The conversion rate of the xylylene dicarbamate in the thermal decomposition is, for example, 80 mol % or more, preferably 90 mol % or more. The conversion rate of the xylylene diisocyanate is determined in conformity with Examples to be described later.

Meanwhile, in the above-described thermal decomposition step, two carbamate groups of the xylylene dicarbamate are thermally decomposed to produce xylylene diisocyanate, and the thermal decomposition liquid may further contain, for example, xylylene monoisocyanate (xylylene monocarbamate) or xylylene dicarbamate.

Then, those compounds having carbamate groups such as xylylene dicarbamate and xylylene monoisocyanate are allowed to react with a compound having an isocyanate group such as xylylene diisocyanate and xylylene monoisocyanate, which may cause, for example, allophanate formation and isocyanurate formation, thereby producing thermal decomposition residues (isocyanate residues (tar component)).

Among all, when the xylylene diisocyanate contains a large amount of impurities, there may be a case where xylylene diisocyanate, xylylene monoisocyanate, xylylene dicarbamate, furthermore, allophanate (allophanate modified product of xylylene diisocyanate), and the like are converted to a high molecular weight product with the impurities as a source, thereby increasing thermal decomposition residues (isocyanate residues (tar component)).

Meanwhile, in the above-described method for producing xylylene diisocyanate, the above-described xylylene dicarbamate is used, so that a production amount of the thermal decomposition residues can be reduced.

To be specific, the xylylene diisocyanate yield relative to the material xylylene dicarbamate is, for example, 80 mol % or more, preferably 90 mol % or more.

The xylylene monoisocyanate yield relative to the material xylylene dicarbamate is, for example, 20 mol % or less, preferably 10 mol % or less.

The allophanate yield relative to the material xylylene dicarbamate is, for example, 10 mol % or less, preferably 5 mol % or less.

The thermal decomposition residues yield relative to the material xylylene dicarbamate is, for example, 5 mol % or less, preferably 1 mol % or less.

In this manner, in the above-described method for producing xylylene diisocyanate, the above-described xylylene dicarbamate having a reduced impurity content is used, so that xylylene diisocyanate can be obtained in high yield.

EXAMPLES

In the following, the present invention is described in further detail with reference to Examples and Comparative Examples, but the present invention is not limited in any way to Examples and Comparative Examples. The values shown in Examples below can be replaced with the corresponding values shown in embodiments (that is, upper limit value or lower limit value).

Test Example 1 (Identification of Impurities)

1,3-xylylene dicarbamate was into a heat-resistant vessel to be subjected to a heating test at 150° C. for 16 hours. Next, the content after the heating test was analyzed with a liquid chromatography/mass spectrometry (LC/MS) device under the conditions shown in Table 1. In this way, the structure of the compound was identified from a mass spectrum of each of the peaks exhibited at a retention time of [4.587], [6.328], [8.588], and [10.187] in a liquid chromatogram.

TABLE 1

| LC Conditions | |
|---|---|
| Device | Manufactured by Nihon Waters K.K. Acquity ™   Binary Solvent Manager   Sample Manager |
| Column | Manufactured by Nihon Waters K.K. Acquity UPLC ™ BEH C8 (2.1 mmID × 100 mm, 1.7 µm) |
| Mobile Phase A | Acetonitrile |
| Mobile Phase B | Aqueous Solution of 5 mM Ammonium Acetate |
| Gradient | A/B = 5/95 to 95/5 to 5/95 0 to 20.8 to 31 to 32 min |
| Strong Wash | 0.5 mL of Acetonitrile |
| Weak Wash | 1.5 mL of 5% Acetonitrile |
| Flow Rate | 0.4 mL/min |
| Column Temperature | 40° C. |
| Injection Amount | 1 µL (Automatic Injection, Partial Loop With Needle Overfill) |
| Detector | Manufactured by Nihon Waters K.K. Acwuity ™   PDA eλ Detector |
| Extracted Wavelength | 220 nm, 254 nm (190 to 400 nm) |
| MS Conditions | |
| Device | Manufactured by Nihon Waters K.K. Xevo G2 Qtof |
| Measurement Mode | ESI (Positove, Negative), m/z = 50-1,000 |
| Capillary | 3.0 kV (Positive, Negative) |
| Extractor | 5 V |
| Source Temperature | 150° C. |
| Desolvation Temperature | 500° C. |
| Cone Gas Flow | 50 L/h |
| Desolvation Gas Flaw | 1000 L/h |

As a result, the compound assigned to the peak exhibited at a retention time of [4.587] was identified as a carboxyl-benzyl carbamate (carboxylic acid product) represented by the above-described formula (2).

The compound assigned to the peak exhibited at a retention time of [6.328] was identified as a carbamoyl-benzyl carbamate (amide product) represented by the above-described formula (4).

The compound assigned to the peak exhibited at a retention time of [8.588] was identified as a formyl-benzyl carbamate (aldehyde product) represented by the above-described formula (1).

The compound assigned to the peak exhibited at a retention time of [10.187] was identified as a carbonyl carbamate-benzyl carbamate (imide product) represented by the above-described formula (3).

Figure 2:
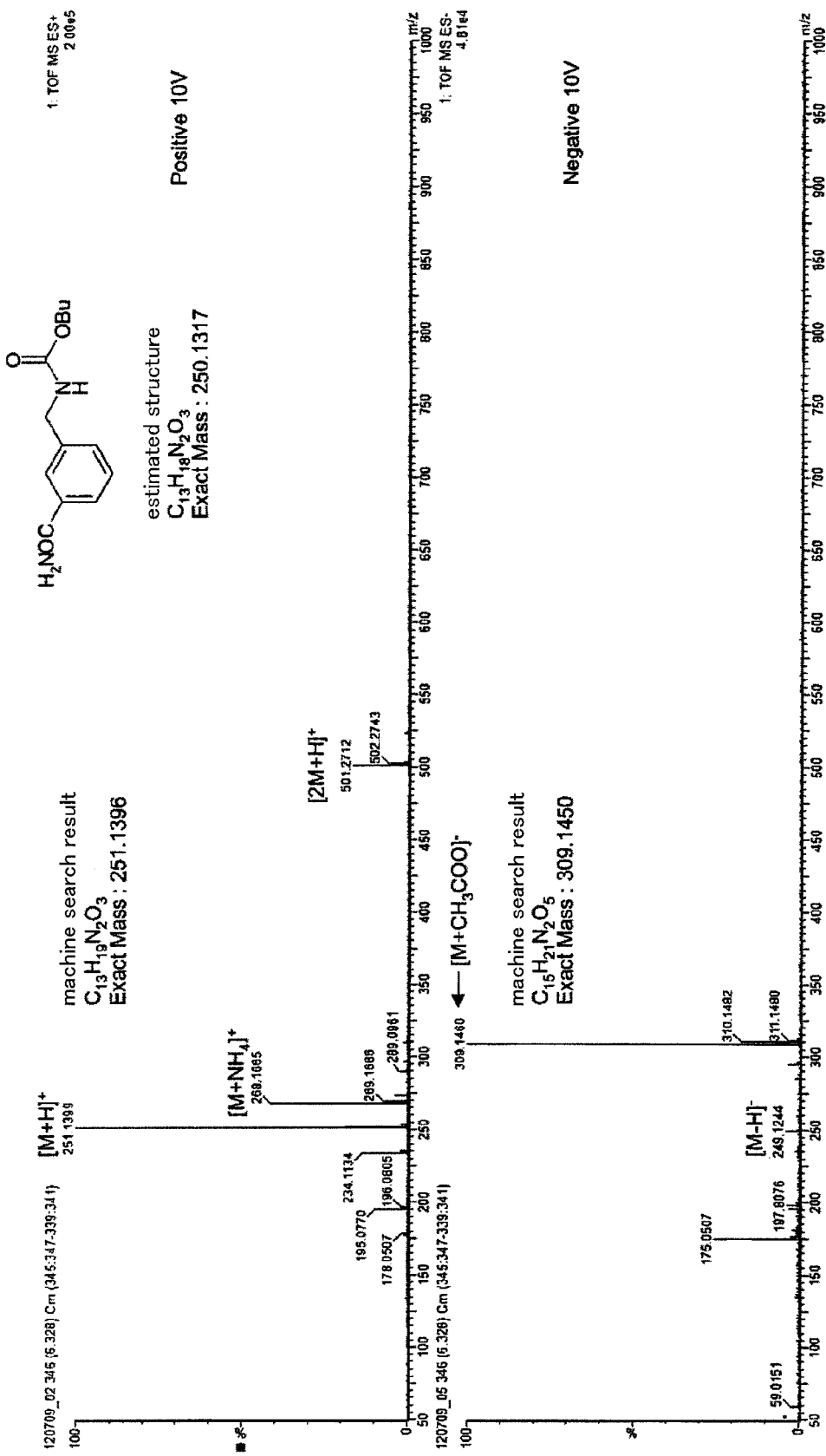
FIG. 2 shows a mass spectrum of the peak exhibited at a retention time of [6.328] in a liquid chromatogram.
Figure 3:
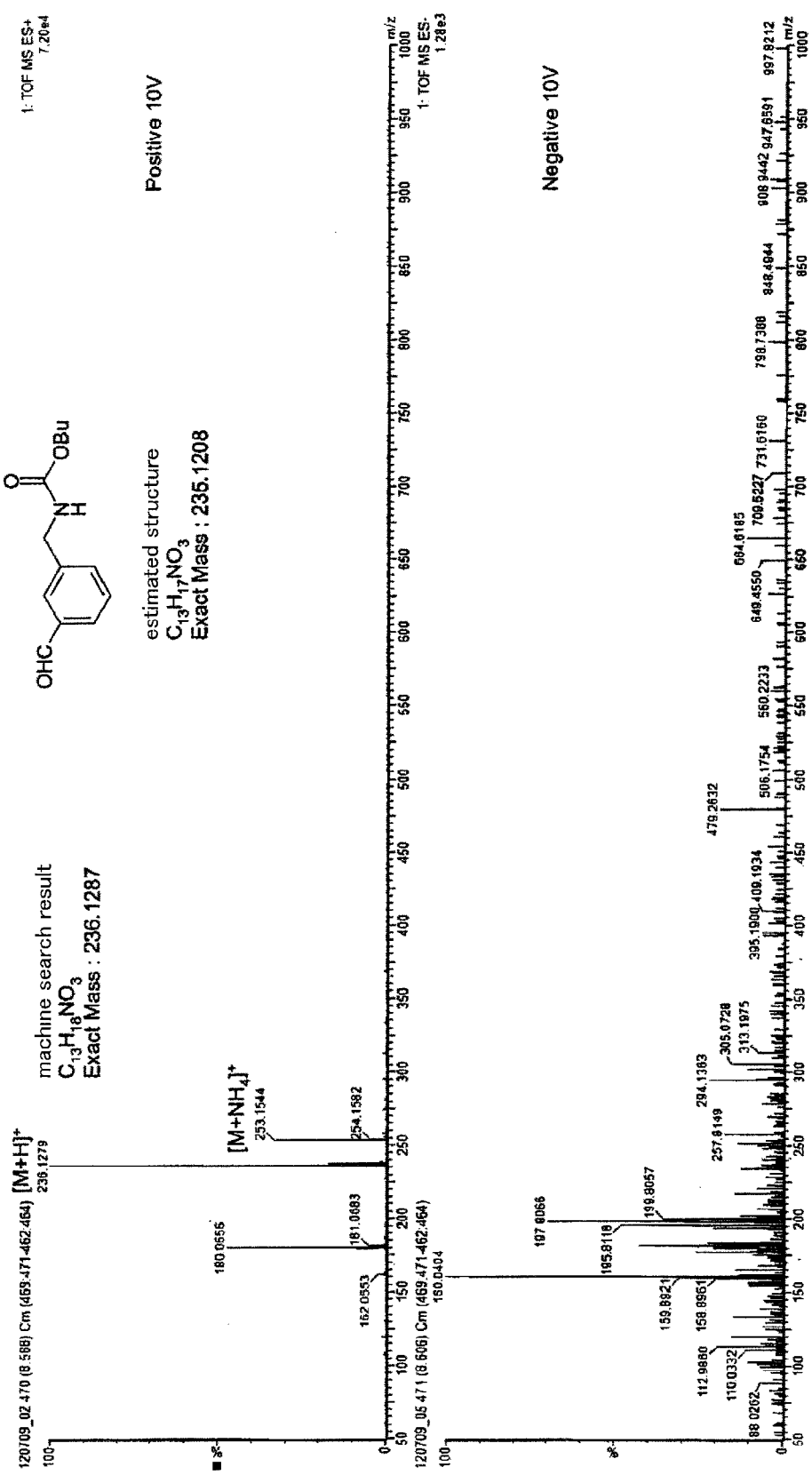
FIG. 3 shows a mass spectrum of the peak exhibited at a retention time of [8.588] in a liquid chromatogram.
Figure 4:
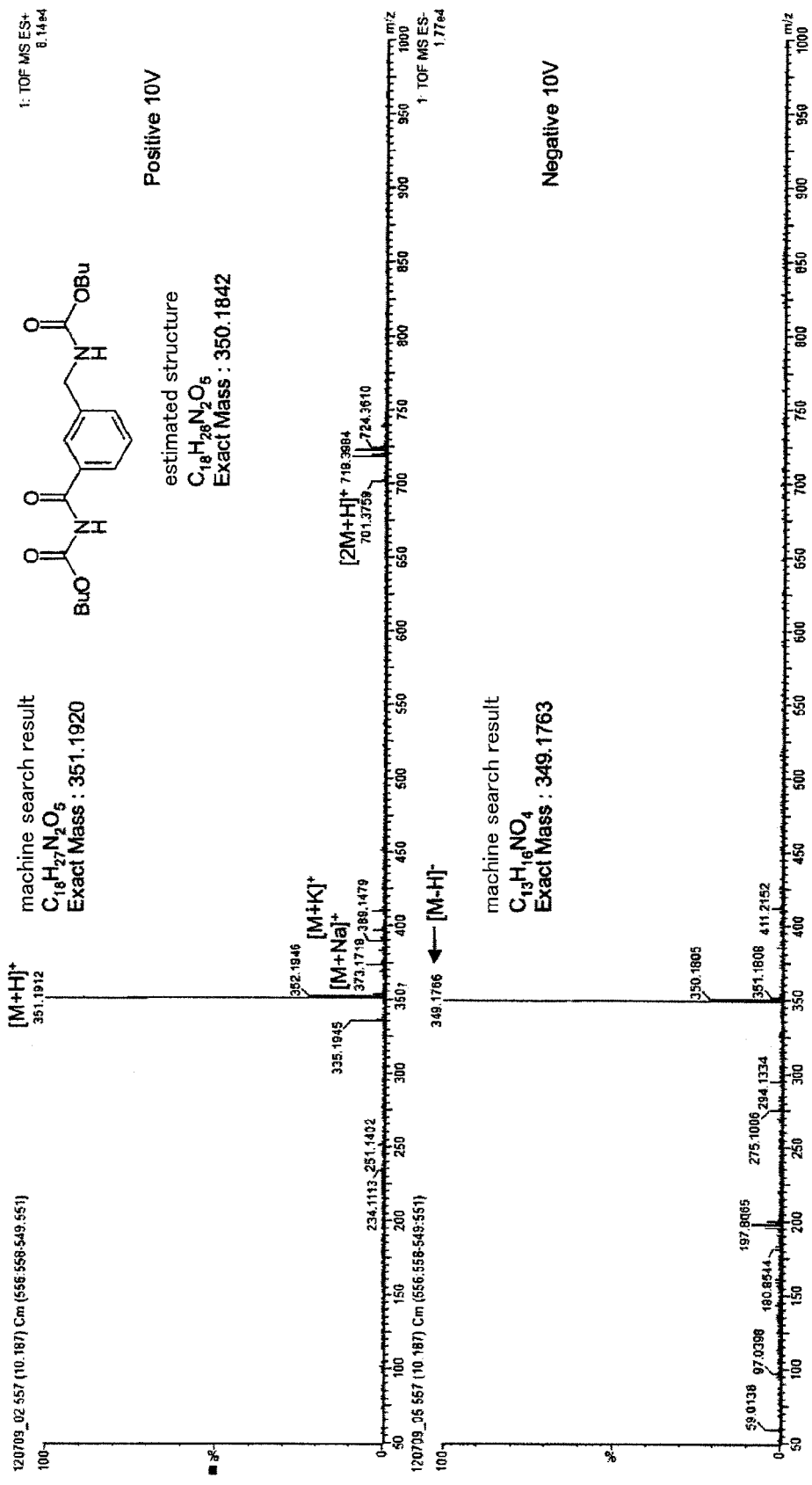
FIG. 4 shows a mass spectrum of the peak exhibited at a retention time of [10.187] in a liquid chromatogram.

The mass spectrum of each of the peaks is shown in FIGS. 1 to 4.

Example 1

<Xylylene Dicarbamate>

1,3-xylylene dicarbamate was put into a heat-resistant vessel and the total amount of impurities (the compound represented by the above-described formulas (1) to (4)) in the 1,3-xylylene dicarbamate was obtained with high performance liquid chromatography. As a result, the impurity content was 0 ppm. A case where the impurity content was less than the detection limit (less than 1 ppm) with the high performance liquid chromatography was defined as 0 ppm (hereinafter, the same).

Next, the above-described heat-resistant vessel was filled with a high-purity nitrogen gas having a purity of 99.999% by volume. At this time, the total oxygen amount of the oxygen amount contained in a space portion of the vessel of the 1,3-xylylene dicarbamate and the oxygen amount dissolved in the xylylene dicarbamate relative to the xylylene dicarbamate was 10 ppm.

The oxygen amount was calculated by measuring a vapor phase portion and a xylylene dicarbamate portion (liquid phase portion) immediately before filling with an oximeter (manufactured by Central Kagaku Corp., DO meter UC-12-SOL type) (hereinafter, the same).

Next, in the heat-resistant vessel, the 1,3-xylylene dicarbamate was stored for 12 hours in a state of being heated at 120° C. Thereafter, the total amount of impurities compound represented by the above-described formulas (1) to (4)) in the 1,3-xylylene dicarbamate was obtained with high performance liquid chromatography. As a result, the impurity content was 10 ppm.

<Xylylene Diisocyanate>

The above-described 1,3-xylylene dicarbamate after storage and dibenzyltoluene as an inert solvent were mixed at a mass ratio of 1 to 1, thereby preparing a material component. Then, 100 ppm relative to the xylylene dicarbamate of p-toluene sulfonamide as a stabilizer was added to the prepared material component.

Thereafter, the above-described material component was continuously fed to a 500 mL interior content glass-made four-neck flask equipped with a stirrer and a rectifying column having a return pipe at the top so that the feeding amount was 120 g/hr, and left there for 5 hours under the conditions of 255° C. and 3.33 kPa (25 torr). In this manner, the xylylene dicarbamate was thermally decomposed and a product containing xylylene diisocyanate and alcohol was obtained. The product contained xylylene monoisocyanate, allophanate, and thermal decomposition residues (tar component).

Then, the product obtained by the above-described thermal decomposition was fed to a condenser having a temperature set to be 80° C. to be partially eliminated as a vapor component, and the remainder was condensed to obtain a condensate.

The xylylene dicarbamate conversion ate in the above-described thermal decomposition reaction determined by the following formula was 99 mol %.

The xylylene diisocyanate yield determined by the following formula relative to the material xylylene dicarbamate was 95 mol %.

The xylylene monoisocyanate yield determined by the following formula relative to the material xylylene dicarbamate was 2 mol %.

The allophanate yield determined by the following formula elative to the material xylylene dicarbamate was 2 mol %.

The tar component yield determined by the following formula relative to the material xylylene dicarbamate was 1 mol %.

xylylene dicarbamate conversion rate=(amount of xylylene dicarbamate−amount of unreacted xylylene dicarbamate)÷amount of xylylene dicarbamate fed×100 xylylene diisocyanate yield=xylylene diisocyanate amount in isocyanate-containing component÷amount of xylylene dicarbamate fed×100 xylylene monoisocyanate yield=xylylene monoisocyanate amount in reaction liquid÷amount of xylylene dicarbamate fed×100 allophanate yield=allophanate amount in reaction liquid÷amount of xylylene dicarbamate fed×100 tar yield=tar amount (xylylene diisocyanate conversion) in reaction liquid÷amount of xylylene dicarbamate fed×100

Example 2

<Xylylene Dicarbamate>

1,3-xylylene dicarbamate was reserved in the same manner as that in Example 1, except that the reserving time was changed to 24 hours. Thereafter, the total amount of impurities (the compound represented by the above-described formulas (1) to (4)) in the 1,3-xylylene dicarbamate was obtained. As a result, the impurity content was 40 ppm.

<Xylylene Diisocyanate>

The above-described xylylene dicarbamate after storage was thermally decomposed to obtain a product containing xylylene diisocyanate and alcohol in the same manner as that in Example 1. Thereafter, the obtained product was partially eliminated as a vapor component and the remainder was condensed to obtain a condensate.

The xylylene dicarbamate conversion rate in the above-described thermal decomposition reaction determined by the same manner as that in Example 1 was 99 mol %.

The xylylene diisocyanate yield determined by the same manner as that in Example 1 relative to the material xylylene dicarbamate was 95 mol %.

The xylylene monoisocyanate yield determined by the same manner as that in Example 1 relative to the material xylylene dicarbamate was 2 mol %.

The allophanate yield determined by the same manner as that in Example 1 relative to the material xylylene dicarbamate was 2 mol %.

The tar component yield determined by the same manner as that in Example 1 relative to the material xylylene dicarbamate was 1 mol %.

Comparative Example 1

<Xylylene Dicarbamate>

1,3-xylylene dicarbamate was reserved in the same manner as that in Example 1, except that an industrial nitrogen gas having a purity of 99.99% by volume was used instead of the high-purity nitrogen gas having a purity of 99.999% by volume. At this time, the total oxygen amount of the oxygen amount contained in a space portion of vessel of the 1,3-xylylene dicarbamate and the oxygen amount dissolved in the xylylene dicarbamate relative to the xylylene dicarbamate was 100 ppm.

Thereafter, the total amount of impurities (the compound represented by the above-described formulas (1) to (4)) in the 1,3-xylylene dicarbamate was obtained. As a result, the impurity content was 100 ppm.

<Xylylene Diisocyanate>

The above-described xylylene dicarbamate after storage was thermally decomposed to obtain a product containing xylylene diisocyanate and alcohol in the same manner as that in Example 1. Thereafter, the obtained product was partially eliminated as a vapor component and the remainder was condensed to obtain a condensate.

The xylylene dicarbamate conversion rate in the above-described thermal decomposition reaction determined by the same manner as that in Example 1 was 99 mol %.

The xylylene diisocyanate yield determined by the same manner as that in Example 1 relative to the material xylylene dicarbamate was 92 mol %.

The xylylene monoisocyanate yield determined by the same manner as that in Example 1 relative to the material xylylene dicarbamate was 2 mol %.

The allophanate yield determined by the same manner as that in Example 1 relative to the material xylylene dicarbamate was 2 mol %.

The tar component yield determined by the same manner as that in Example 1 relative to the material xylylene dicarbamate was 4 mol %.

Comparative Example 2

<Xylylene Dicarbamate>

1,3-xylylene dicarbamate was reserved in the same manner as that in Comparative Example 1, except that the reserving time was changed to 24 hours. Thereafter, the total amount of impurities (the compound represented by the above-described formulas (1) to (4)) in the 1,3-xylylene dicarbamate was obtained. As a result, the impurity content was 350 ppm.

<Xylylene Diisocyanate>

The above-described xylylene dicarbamate after storage was thermally decomposed to obtain a product containing xylylene diisocyanate and alcohol in the same manner as that in Example 1. Thereafter, the obtained product was partially eliminated as a vapor component and the remainder was condensed to obtain a condensate.

The xylylene dicarbamate conversion rate in the above-described thermal decomposition reaction determined by the same manner as that in Example 1 was 99 mol %.

The xylylene diisocyanate yield determined by the same manner as that Example 1 relative to the material xylylene dicarbamate was 91 mol %.

The xylylene monoisocyanate yield determined by the same manner as that in Example 1 relative to the material xylylene dicarbamate was 2 mol %.

The allophanate yield determined by the same manner as that in Example 1 relative to the material xylylene dicarbamate was 2 mol %.

The tar component yield determined by the same manner as that in Example 1 relative to the material xylylene dicarbamate was 5 mol %.

Reference Example 1

<Xylylene Dicarbamate>

The total amount of impurities (the compound represented by the above-described formulas (1) to (4) in the 1,3-xylylene dicarbamate was obtained in the same manner as that in Comparative Example 1, except that the 1,3-xylylene dicarbamate was used without being heated and reserved. As a result, the impurity content was 0 ppm.

<Xylylene Diisocyanate>

The above-described xylylene dicarbamate before heating and storage was thermally decomposed to obtain a product containing xylylene diisocyanate and alcohol in the same manner as that in Example 1. Thereafter, the obtained product was partially eliminated as a vapor component and the remainder was condensed to obtain a condensate.

The xylylene dicarbamate conversion rate in the above-described thermal decomposition reaction determined by the same manner as that in Example 1 was 99 mol %.

The xylylene diisocyanate yield determined by the same manner as that in Example 1 relative to the material xylylene dicarbamate was 95 mol %.

The xylylene monoisocyanate yield determined by the same manner as that in Example 1 relative to the material xylylene dicarbamate was 2 mol %.

The allophanate yield determined by the same manner as that n Example 1 relative to the material xylylene dicarbamate was 2 mol %.

The tar component yield determined by the same manner as that in Example 1 relative to the material xylylene dicarbamate was 1 mol %.

The results of Examples and Comparative Examples are shown in Table 2.

TABLE 2

| No. | $N_2$ Purity (% by volume) | $O_2$ Concentration (ppm) | XDC Reserving Conditions | | XDC | | | | | |
|---|---|---|---|---|---|---|---|---|---|---|
| | | | Heating Temperature (° C.) | Heating Time (hour) | Impurity Content (ppm) | XDC Conversion Rate (mol %) | XDI Yield (mol %) | XMI Yield (mol %) | Allophanate Yield (mol %) | Tar Yield (mol %) |
| Ex. 1 | 99.999 | 10 | 120 | 12 | 10 | 99 | 95 | 2 | 2 | 1 |
| Ex. 2 | 99.999 | 10 | 120 | 24 | 40 | 99 | 95 | 2 | 2 | 1 |
| Comp. Ex. 1 | 99.99 | 100 | 120 | 12 | 100 | 99 | 92 | 2 | 2 | 4 |
| Comp. Ex. 2 | 99.99 | 100 | 120 | 24 | 350 | 99 | 91 | 2 | 2 | 5 |
| Ref. Ex. 1 | 99.99 | 100 | — | — | 0 | 99 | 95 | 2 | 2 | 1 |

The abbreviations in the Table are shown below.
XDC: xylylene dicarbamate
XDI: xylylene diisocyanate
XMT: xylylene monoisocyanate While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

INDUSTRIAL APPLICABILITY

Xylylene dicarbamate, a method for producing xylylene diisocyanate using the xylylene dicarbamate, xylylene diisocyanate obtained by the method for producing xylylene diisocyanate, and a method for reserving xylylene dicarbamate capable of reducing an impurity content of the present invention can be, for example, widely used in various industrial fields using xylylene dicarbamate and xylylene diisocyanate such as a material of medicine, agricultural chemicals, and the like; a material of various fine chemicals; an analysis agent of alcohols; and a production material of an isocyanate.

The invention claimed is:

1. Xylylene dicarbamate containing:
impurities represented by formulas (1) to (4) below at a ratio of less than 100 ppm as a total amount thereof on a mass basis

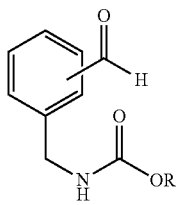
(1)

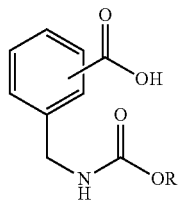
(2)

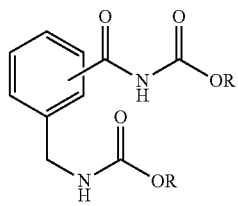
(3)

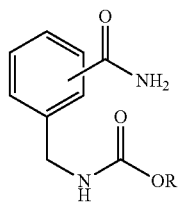
(4)

in the above-described formulas (1) to (4), R represents a monovalent hydrocarbon group.

* * * * *